United States Patent [19]

Zacharias

[11] Patent Number: 4,596,136
[45] Date of Patent: Jun. 24, 1986

[54] METHOD OF DETERMINING THE NET VOLUME OF WATER AND OIL IN A FLOW STREAM

[75] Inventor: Ellis M. Zacharias, Tulsa, Okla.

[73] Assignee: Nusonics, Inc., Tulsa, Okla.

[21] Appl. No.: 700,609

[22] Filed: Feb. 11, 1985

[51] Int. Cl.[4] ............................................. G01N 29/02
[52] U.S. Cl. .............................. 73/61.1 R; 73/861.04
[58] Field of Search ..................... 73/53, 61 R, 61.1 R, 73/597, 861.04

[56] References Cited

U.S. PATENT DOCUMENTS

| | | | |
|---|---|---|---|
| 3,892,127 | 7/1975 | Cirulis et al. | 73/61.1 |
| 4,080,837 | 3/1978 | Alexander et al. | 73/61.1 |
| 4,236,406 | 12/1980 | Reed et al. | 73/61.1 |

*Primary Examiner*—Herbert Goldstein

*Attorney, Agent, or Firm*—Head, Johnson & Stevenson

[57] ABSTRACT

A method of determining the net volume of water and oil in a flow stream including the steps of measuring the gross volume of fluid flowing in the stream, periodically collecting from the stream samples of the oil and water mixture, treating each sample of the oil and water mixture to cause any entrained gas bubbles to be absorbed in the mixture or reduced to selected maximum size and entrained emulsion droplets are reduced in size, passing the treated sample of oil and water mixture through a sonic apparatus, measuring the speed of sound transmission of the mixture within the sonic apparatus and determining from the speed of sound transmission the relative composition of water and oil in the mixture, and calculating the gross volumetric oil and water utilizing the measurements obtained from the sonic apparatus and from the measurement of the gross volume of fluid.

14 Claims, 1 Drawing Figure

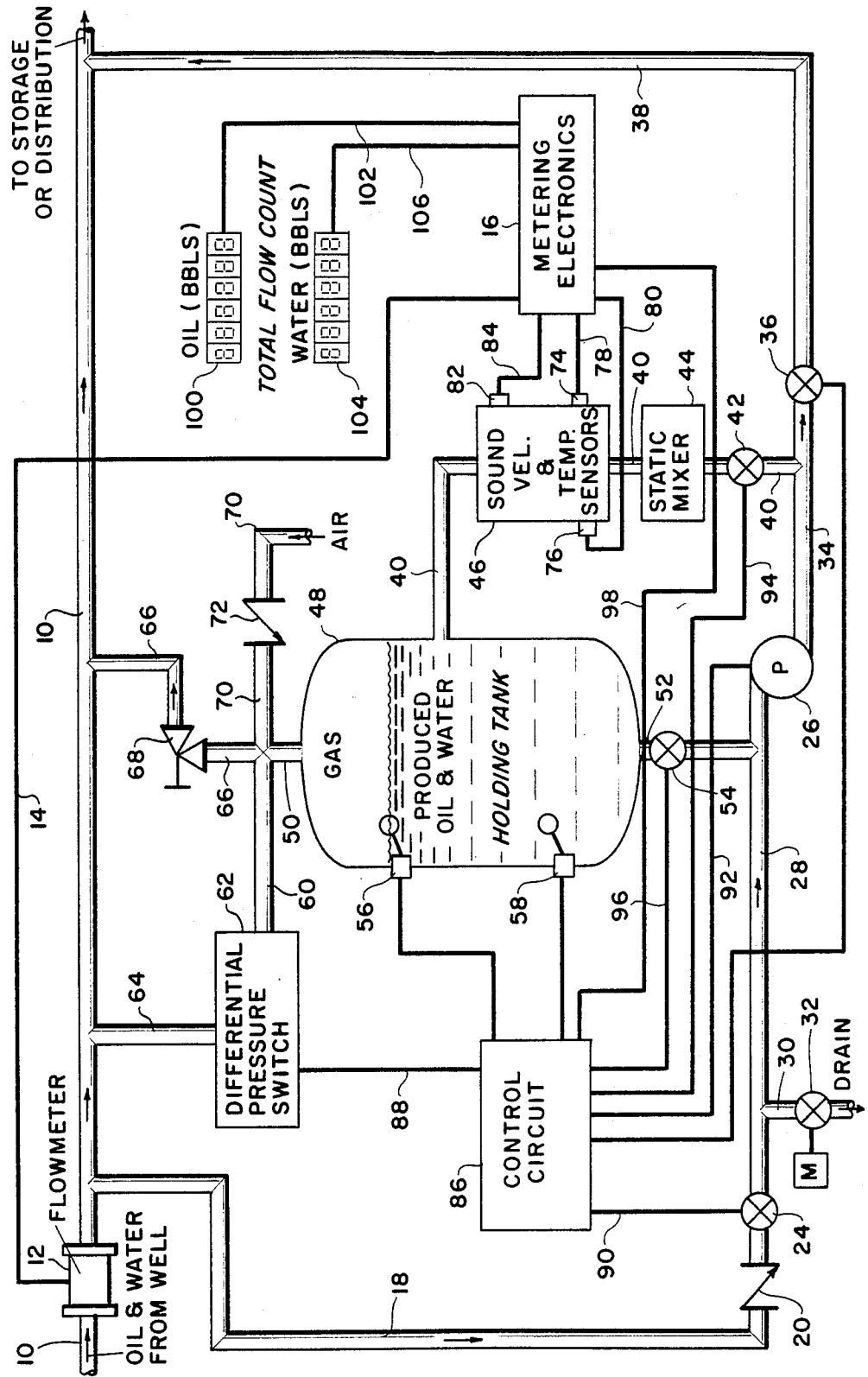

METHOD OF DETERMINING THE NET VOLUME OF WATER AND OIL IN A FLOW STREAM

SUMMARY OF THE INVENTION

In the petroleum industry, as well as in other processing and chemical industrial applications, it is frequently necessary to be able to accurately determine in a stream flow the net amount of different components of the stream. In the petroleum industry it is frequently desirable to determine the net volume of water and oil making up the stream.

One method of determining whether a stream is made up of water or oil employs the use of a sonic apparatus. It is well known that the speed of sound transmission of water and oil are different and by measuring the speed of sound transmission of fluid flow in a stream the amount of water and oil making up the stream can be determined.

Others have applied the principle of the use of the speed of sound transmission to detect the transition in a fluid stream of oil to water or water to oil such as in previously issued U.S. Pat. Nos. 4,236,406 and 4,080,837. One problem however, which has existed with the present methods and apparatus, is that most crude oil includes co-mingled gas which may be in the form of entrained bubbles. While sonic apparatus works efficiently and effectively to measure the speed of sound transmission in liquids and can be used to readily distinguish between water and oil when the liquids are relatively gas free, the presence of gas in the stream can materially affect the measurements provided by the sonic apparatus. When gas is entrained in the liquid the sonic measurements may lead to inconclusive or erroneous indications. Since gas is so characteristically present in crude oil the existence of entrained gas bubbles in crude oil, or in water associated with crude oil, can jeopardize the dependability of measurements made by sonic apparatus.

The invention is directed towards an improved method of determining liquid composition in a flow stream. A flow meter, which may be of the mechanical type, measures the gross volumetric flow of an oil and water mixture in a pipe line. Periodically, a sample of the mixture is extracted from the pipe line and passed into a tank.

The composition of the mixture is determined by measuring the speed of sound transmission. There are primary problems in sonic measurements of a water and oil mixture as typically found in the petroleum industry, that is, entrained gas and emulsion droplets. When either gas bubbles or emulsion droplets exist of sizes large compared to the wavelength of the sonic energy used, the bubbles and/or droplets will cause refraction, diffraction and scattering of the sonic energy and thus the accuracy of the sonic measurements is impaired. Typically it is desirable to reduce the size (diameter) of bubbles or emulsion droplets until they are smaller than one tenth of a wavelength of the ultrasonic pressure wave or until the bubbles occupy a volume less than 0.1 percent of the liquid volume. When using an ultrasonic frequency of one megahertz, the wavelength in water, for which the sound speed is approximately 1500 meters per second, is 0.0015 meters or 0.059 inches. Thus the bubble or emulsion droplet size should be less than 150 micrometers or 0.006 inches.

To overcome the problem of entrained gas, pressure is applied to the mixture in the tank to cause entrained gas to be forced into solution.

To reduce the maximum emulsion droplet size, the sample liquid is recirculated by a gear pump or other apparatus, where shear action serves to reduce the size of droplets. A static mixer may be used to increase the shearing action. During recirculation, sound velocity measurements may be repeatedly made. The recirculation continues until the sound velocity measurements stabilize. In another method, the attenuation of sound transmission in the mixture is measured as the mixture is circulated. Circulation is continued until the attenuation, which is indicative of the amount of entrained emulsion droplets having sizes which interfere with the transmission of sound, is reduced to a pre-selected level. Thereafter, the speed of sound transmission measurement is taken as a means of determining the relative composition of the mixture.

After a relative composition has been determined the sample is passed back into the pipeline or discharged into a storage tank. On a periodic basis samples are repeatedly taken and by combining the measurements of the mechanical flowmeter and that of the sonic determination of the relative composition of the oil and water mixture, the gross amounts of oil and water flowing through the pipeline can be determined. By measuring temperature and correcting for volume expansion, the net oil and water may be determined.

BRIEF DESCRIPTION OF THE DRAWING

FIG. 1 diagrammatically illustrates a method of measuring the oil and water flowing as a mixture in a pipeline in which periodic samples of the mixture are taken. The samples are conditioned to decrease the deleterious effect of emulsions and entrained gas and the proportion of oil and water in the mixture is determined by measuring the speed of sound transmission of the conditioned mixture.

DESCRIPTION OF THE PREFERRED EMBODIMENT

Referring to FIG. 1, the numeral 10 designates a pipeline which, by example, may be connected to one or more producing oil wells carrying a mixture of oil and water produced by the oil wells, or the pipeline may be connected to an intermediate gas removal gravity separator tank. The oil and water mixture flowing through pipeline 10 flows through a meter 12. While the meter 12 may be a sonic, orifice plate, magnetic, ventura or other type of flow meter, it preferably may be a mechanical type, that is, a positive displacement flow meter or turbine type which responds accurately to fluid flow, irrespective of whether the fluid is oil or water so that the gross volume of fluid flowing in pipeline 10 is determined. By way of conductor 14 the gross volume measurement of meter 12 is conveyed to a metering electronics console 16.

The flow meter 12 gives the operator information as to the total volume of fluid flow but does not give information as to the total volume of oil and the total volume of water in the stream. The purpose of this invention is to provide such information to the operator. For this purpose, samples of the fluid are periodically extracted from the pipeline 10 and the proportion of the oil and gas water content of the sample is determined. This information is utilized in conjunction with the gross volume flow as measured by meter 12.

First the structure which is illustrated in FIG. 1 will be described as it is exemplary of apparatus which can be employed to practice the invention. Thereafter, the methods by which the structure and apparatus is used to measure the composition of an oil and water mixture making up the flow stream in pipeline 10 will be described. Connected to pipeline 10 is a conduit 18 by which samples of fluid can be extracted from the pipeline. Conduit 18 connects through a check valve 20 and through a control valve 24. A conduit 28 extends from control valve 24 to the inlet of a pump 26 and has a connecting portion 30 with a manually operated drain valve 32. Valve 32 is utilized only to drain the entire system and is not normally employed in making measurements of oil and water.

A conduit 34 extends from the outlet of pump 26 to a control valve 36. Conduit 38 extends from the control valve back to pipeline 10.

Extending from conduit 34 is a branch conduit 40 which passes through a control valve 42, a static mixer 44 and a sound velocity and temperature station 46. From station 46 the conduit extends to a small pressure vessel 48.

The pressure vessel may be of approximately two gallon size although the actual volume is not directly material to the practice of the invention. Vessel 48 has communciation with an upper conduit 50 and a lower conduit 52 which connects through a control valve 54 back to conduit 28. Upper and lower fluid level detectors 56 and 58 respectively are positioned within vessel 48 to provide electrical signals responsive to the level of fluid within the tank.

Conduit 50 extending from the upper end of vessel 48 branches four ways, one branch being conduit 60 to a differential pressure switch 62 which also has communication by conduit 64 back to pipeline 10. The differential pressure switch provides an electrical signal responsive to the pressure difference between the interior of vessel 48 and pipeline 10. One of the branches from conduit 50 extends by way of conduit 66 to a pressure relief valve 68. The extension of conduit 66 connects the pressure relief valve 68 to pipeline 10. The final branch from conduit 50 extending from the upper end of the vessel 48 is by conduit 70 through a check valve 72 to atmosphere. Valve 72 permits air to flow only into vessel 48 but does not permit flow of gas or liquids out.

The sound velocity and temperature sensor station 46 includes opposed sonic transducers 74 and 76 by which the velocity of sound in the fluid flowing through station 46 can be determined. Conductors 78 and 80 connect the transducers to metering electronics 16. Also positioned in the sound velocity and temperature station 46 is a temperature sensor 82 which connects to metering electronics 16 by conductor 84.

A control circuit 86 provides signals for operation of the valves in response to input information. The following conductors convey signals from or transmit signals to control circuit 86: conductor 88 from the pressure differential switch 62; conductor 90 to control valve 24; conductor 92 to pump 26; conductor 94 to control valve 42; and conductor 96 to control valve 54. In addition, conductor 98 connects the control circuit 86 with the metering electronics 16. While the control circuit 86 and metering electronics 16 are illustrated as separate portions of the apparatus this is for simplifying the drawing only and in normal applications these elements will be combined into a single electronics package.

The results of the measurements from metering electronics 16 provide indications of the total volumetric oil on register 100, connected to metering electronics by conductor 102, and water on register 104, connected by conductor 106. The entire apparatus of the drawing can be assembled in a unitary package and, if desired, be skid mounted for easy movement from one location to another as required by the user.

DESCRIPTION OF THE METHOD OF PRACTICING THE INVENTION

The sequence of steps by which the apparatus of the drawing can be employed to practice the method of this invention will be easier to understand with reference to the following charts wherein the letter "S" designated a valve shut and the letter "O" designates the valve open.

| | Valve and Pump Status | | | | |
|---|---|---|---|---|---|
| | VALVE 24 | VALVE 42 | VALVE 36 | VALVE 54 | PUMP 26 |
| Not Operating | S | S | S | S | OFF |
| Flushing Cycle | O | S | O | S | ON |
| Filling Cycle | O | O | S | S | ON |
| Measurement Cycle | S | O | S | O | ON |
| Emptying Cycle | S | S | O | O | ON |

When the device is not in use all of the valves are shut. For this reason, control valves 24, 42, 36 and 54 may be of the type which are normally closed and are opened by application of electrical signals. Pump 26 is off, that is, non-energized. Thus in the non-operating condition electrical current is employed only by metering electronics 16 as necessary to receive and store input from flow meter 12. An operating sequence can be initiated on a selected periodic basis which can be automatically accomplished by means of a clock (not illustrated) within the electronics. Typically, a measuring sequence may be employed once every 10 minutes or less frequently if the apparatus is used in an environment in which the oil and water ratio changes only slowly. On the other hand if the oil and water ratio is apt to change more rapidly the measuring sequence can be arranged to be repeated almost continuously so that when one operating sequence is completed another one can begin immediately. Since the time of an operating sequence will typically be only about one minute or so, the sequences can be completed very often if necessary.

When an operating sequence begins the first step is a flushing cycle, the purpose of which is to flush out of the piping old oil and water from the previous sequence so that each new sequence measures the ratio of oil and water from a separate and independently taken sample of fluid from pipeline 10. On signal from control circuit 86, valves 24 and 36 open, after which pump 26 is turned on. By means of pump 26 fluid in the conduits 18, 28, 34, and 38 is completely flushed out and delivered back to pipeline 10. After this predetermined sequence, set by a preselected time interval, the next sequence, that is the filling sequence, begins.

To start the filling sequence, valve 42 opens after which valve 36 shuts. Pump 26 continues to run and now delivers product from the conduits 18 and 28, through conduit 34 and valve 42, and through conduit 40 into vessel 48, the flow passing through the static mixer 44 and the sound velocity and temperature station 46. Pumping continues until the desired level and pressure of fluid is reached in the vessel 48. This is indicated by a signal from the upper level sensor 56 and the desired pressure as detected by differential pressure switch 62. Typically, the desired pressure will be selected to be in the 75 to 90 psi range. The filling sequence will continue until both a selected liquid level is reached as detected by level control 56 and a preselected pressure in tank 48 is achieved. If the fluid being sampled has a less than usual gas content, which gas is compressed as the vessel 48 is filled, the level reached before the selected differential pressure switch 62 actuates may cause the fluid level to rise above level control 56, which event is satisfactory. The only requirement is that the vessel be filled to the level indicated by 56 or above, and that the differential pressure of the contents of the vessel 48 relative to pipeline 60 is at the preselected level.

The filling sequence serves two basic purposes. First, it extracts a sample of the fluid flowing in vessel 10 so that a measurement can be made as to the oil and water ratio. Second, by filling the vessel 48 to a high maximum differential pressure gas entrained with the liquid will be forced into solution. As previously indicated, the measurement of speed of sound transmission in a liquid is jeopardized if gas bubbles exist of large size and frequency in the sampling fluid. By elevating the pressure to the range of 75 to 90 psi the entrained gas in the liquid will be forced into solution thereby any remaining bubbles will be of a size so as not to interfere with measurements of the sound velocity as will be hereinafter described.

After the filling sequence has been completed, the next step is the measurement cycle, which actually employs two sequences, the first sequence is to reduce emulsion droplets to an acceptable level, and the second sequence is to measure the oil and water content of the fluid. For this purpose valve 54 opens and immediately thereafter valve 24 shuts. Valve 24 is shut so that no further fluid is extracted from pipeline 10. Valve 42 remains open and valve 36 remains shut so that the extracted sample is captured between valves 24 and 36 and concentrated within vessel 48. Valve 54, permitting fluid to flow from vessel, is opened. Pump 26 continues to run. When valve 54 opens fluid is cycled from the vessel, through pump 26, valve 42, static mixer 44, sound velocity and temperature sensor station 46 and back into the interior of the vessel. Recycling of the sample fluid is continued for a period of time. As has been previously discussed, one problem in measuring the speed of sound transmission of an oil and water mixture is the common inclusion of emulsion droplets. These droplets, when of large size and predominance, refract and scatter sonic energy so that accurate measurements are difficult. By circulating the fluid for a preselected time the emulsion droplets are broken and reduced in size so as to be inconsequential. The emulsion droplets are broken and reduced in size primarily by shear action which can be accomplished in two ways. First, pump 26 is preferably of a type which produces high shear action on the fluid being pumped by it. Therefore, pump 26 may preferably be a gear pump or some equivalent type. A second and additional means of improving shear action is by the use of static mixer 44. These mixers are well known in industry and function by turbulence and shear action to break down emulsion droplets.

The recirculation action can be timed in three different ways. First, it can be for a preselected time. A second method is to constantly monitor the velocity of sound transmission during fluid circulation. As circulation continues the interference from emulsion droplets will decline, thereby reducing the variations in the measured speed of sound transmission of the fluid. By means of electronics 16 it can be determined when the detected speed of sound transmission is stabilized, indicating that the quantity of interfering emulsion droplets has been reduced to the minimum, or near the minimum, achievable under the existing conditions.

Another method of controlling the duration of the recirculation cycle is by measuring attenuation of sound. When emulsion droplets are concentrated in the fluid flowing past transducers 74 and 76, the sound transmitted from one transducer and received by the other is diminished. As the emulsion droplets are broken down into sizes sufficiently small so as not to interfere with the sound transmission, the attenuation decreases. Thus, by measuring attenuation the recirculation step can be continued until a preselected level of attenuation is received. After the recirculation cycle has been completed as determined by one of the three methods above described, the measurement cycle is initiated. Actually the measuring cycle is substantially immediately completed upon the termination of the recirculation cycle and is achieved by measuring the speed of sound transmission utilizing transducers 74 and 76, and electronics 16. Simultaneously the temperature of the fluid is detected by element 82 and this information employed electronically in determining the gross volumes. Utilizing the gross flow measurements from meter 12 the total oil and water flowing through the pipeline can be automatically calculated. For instance, if the apparatus indicates from an average of samples taken repeatedly over a long period, such as a twenty-four hour period, that the fluid flowing through pipeline 10 is forty per cent (40%) water and sixty per cent (60%) oil and if the total volumetric flow detected by meter 12 is 100 barrels then register 104 would show a total volume of 40 barrels of water and register 100 would show a total of 60 barrels of oil. As the total volumetric flow rate changes and the ratio of water and oil changes, the volumetric measurements will be continuously updated.

After the measurement cycle the next is the emptying cycle. This is initiated by electronics upon indication that the measurement step is complete. Valves 54 and 36 open and valve 24 and valve 42 are shut. Pump 26 continues to run and will pump the fluid from within vessel 48 and conduit 28 back to the pipeline 10 through conduit 34 and 38. Since only a known volume is always emptied from each cycle the pumping cycle can be controlled by a preselected time or until low fluid level 58 indicates that substantially all the fluid has been pumped from vessel 48. At the conclusion of the emptying cycle, whether after a selected time or as indicated by float switch 58, the pump is stopped and all valves are shut. Meanwhile, the volume of fluid flowing through meter 12 is continuously recorded and the ratio of oil and water as determined by the most recent sample is used to accumulate the total volume of water and oil flowing through the pipeline 10.

During the emptying cycle it is important that vessel 48 be nearly completely empty and for this reason it is undesirable that a vacuum be imposed which would restrict the drainage of fluid from the vessel. If drainage of fluid from vessel 48 causes subatmospheric pressure in the vessel, check valve 72 allows air to enter the vessel. The vessel can be completely emptied so that the emptying cycle is terminated after preselected time or, if desired, the vessel 48 can be emptied down to the low level control 58 at which time the emptying cycle terminates as previously described. If the vessel is to be completely emptied at the end of each measuring cycle, including piping 52, the use of the low level control 58 is not necessary in the practice of the invention.

The invention described provides a system and method of operation which can be employed to make volumetric measurements of oil and water flowing in a mixed stream. The system utilizes the speed of sound transmission for determining the oil and water ratio and provides means of overcoming the deleterious effect of entrained gas and emulsion droplets normally encountered in oil and water mixtures.

While the invention has been described with a great degree of particularity it is manifest that many changes may be made in the details of construction and the arrangement of components without departing from the spirit and scope of this disclosure. It is understood that the invention is not limited to the embodiment set forth herein for purposes of exemplification, but is to be limited only by the attached claim or claims, including the full range of equivalency to which each step thereof is entitled.

What is claimed is:

1. A method of measuring the composition of an oil and water mixture having entrained gas comprising:
   collecting at least a sample of the mixture in a pressure vessel;
   pressuring the mixture within the vessel to a superatmospheric pressure to force most of the entrained gas into solution and to compress remaining entrained gas bubbles to a preselected maximum size;
   passing the mixture from the vessel while subjected to superatmospheric pressure through a sonic apparatus; and
   measuring the speed of sound transmission of the mixture which speed of sound transmission is indicative of the composition of the mixture flowing through the apparatus.

2. The method of claim 1 including the step of subjecting the pressurized sample of the mixture to shearing action to reduce the size of any entraining emulsion droplets before the step of measuring the speed of sound transmission.

3. The method of claim 2 including the step of:
   rapidly recirculating the mixture from the pressure vessel while under pressure to thoroughly mix the oil and water content and to reduce the size of emulsion droplets until the diameters thereof are small compared to the wavelength of the frequency of the acoustic signal used in the sonic measuring apparatus.

4. A method of measuring the volumetric composition of an oil and water mixture having gas entrained therein, flowing in a pipeline, the mixture comprising:
   (a) measuring the gross volume of the mixture flowing in the pipeline;
   (b) periodically collecting from the pipeline a sample of the mixture;
   (c) treating the sample of the mixture to cause any entrained gas to be at least substantially absorbed in the mixture and any remaining bubbles thereof to be reduced to a selected maximum size;
   (d) passing the treated sample of the mixture through a sonic apparatus;
   (e) measuring the speed of sound transmission of the mixture within the sonic apparatus;
   (f) determining from the speed of sound transmission the relative composition of oil and water in the mixture; and
   (g) calculating the gross volumetric oil and water flowing through the pipeline utilizing the measurements obtained from steps (a) through (f).

5. The method of claim 4 including the step of measuring the temperature of the mixture and utilizing the temperature measurement in the step of calculating the gross volumetric oil and water flowing through the pipeline.

6. The method of claim 4 wherein the sample of oil and water mixture is treated in step (c) to reduce the size of bubbles of gas to a maximum diameter which is small compared to the wavelength of acoustic energy employed in step (e).

7. The method of claim 4 wherein the sample oil and water mixture is treated in step (c) by subjecting the oil and water mixture to superatmospheric pressure, steps (d) and (e) being carried out under such superatmospheric pressure.

8. The method of claim 4 wherein the sample oil and water mixture is treated in step (c) to reduce gas bubbles in the mixture to a volume of less than about 0.1 percent (%) of the volume of the mixture.

9. The method of claim 4 wherein the sample oil and water mixture is treated in step (c) by circulating the mixture employing a pump which accomplishes shear action to reduce the size of any emulsion droplets which might be entrained in the mixture.

10. The method of claim 9 wherein the sample oil and gas mixture is treated in step (c) by circulating the mixture through a sonic apparatus, and including the step of periodically measuring the speed of sound transmission of the mixture, and continuing to circulate the mixture until the measured speed of sound transmission has stabilized.

11. The method of claim 9 wherein the mixture is circulated through a static mixer in series with the sonic apparatus.

12. The method of claim 9 wherein the sample oil and gas mixture is treated in step (c) by circulating the mixture through a sonic apparatus, and including the step of periodically measuring the attenuation of sound transmission in the mixture, and continuing to circulate the mixture until the measured attenuation has reached a preselected minimum.

13. The method of claim 12 wherein the mixture is circulated through a static mixer in series with the sonic apparatus.

14. The method of claim 4 including measuring the temperature of the mixture and employing such temperature measurement in step (f).

* * * * *